US011166821B2

(12) United States Patent
Sazy

(10) Patent No.: US 11,166,821 B2
(45) Date of Patent: Nov. 9, 2021

(54) IMPLANTS AND IMPLANTATION TECHNIQUES FOR SACROILIAC JOINT FUSION

(71) Applicant: John Anthony Sazy, Fort Worth, TX (US)

(72) Inventor: John Anthony Sazy, Fort Worth, TX (US)

( * ) Notice: Subject to any disclaimer, the term of this patent is extended or adjusted under 35 U.S.C. 154(b) by 178 days.

(21) Appl. No.: 16/686,187

(22) Filed: Nov. 17, 2019

(65) Prior Publication Data

US 2020/0155324 A1 May 21, 2020

Related U.S. Application Data

(60) Provisional application No. 62/769,489, filed on Nov. 19, 2018.

(51) Int. Cl.
*A61F 2/30* (2006.01)
*A61F 2/44* (2006.01)

(52) U.S. Cl.
CPC ...... *A61F 2/30988* (2013.01); *A61F 2/30771* (2013.01); *A61F 2/4455* (2013.01); *A61F 2002/30156* (2013.01); *A61F 2002/30405* (2013.01); *A61F 2002/30507* (2013.01); *A61F 2002/30772* (2013.01); *A61F 2002/30995* (2013.01)

(58) Field of Classification Search
CPC ........ A61F 2/30988; A61F 2002/30995; A61F 2/4455
See application file for complete search history.

(56) References Cited

U.S. PATENT DOCUMENTS

| 6,053,916 | A | * | 4/2000 | Moore | A61F 2/30988 |
| | | | | | 606/86 R |
| 6,648,915 | B2 | | 11/2003 | Sazy | |
| 8,454,618 | B2 | | 6/2013 | Stark | |
| 8,979,928 | B2 | | 3/2015 | Donner | |
| 9,119,732 | B2 | | 9/2015 | Schifano | |
| 9,615,856 | B2 | | 4/2017 | Arnett | |
| 9,668,781 | B2 | * | 6/2017 | Stark | A61B 17/8625 |

(Continued)

FOREIGN PATENT DOCUMENTS

WO 2013166496 A1 11/2013

OTHER PUBLICATIONS

International Search Report and Written Opinion, dated Jan. 29, 2020 in PCT/US2019/061958.
Zyga Symmetry Brochure Rev D, Zyga Technology, Inc., © 2015.

*Primary Examiner* — Christian A Sevilla
(74) *Attorney, Agent, or Firm* — The Culbertson Group, P.C.; Russell D. Culbertson

(57) ABSTRACT

A sacroiliac joint implant includes an implant structure formed from an elongated base member, an elongated first side member, and an elongated second side member, with an internal support structure extending in an implant plane from the base member to each of the first side member and the second side member. Three or more fusion passages are defined in an area between the base member, first side member, and second side member. Each fusion passage defines a respective open area through the implant to facilitate bone growth across the sacroiliac joint when the implant is properly implanted in the joint.

19 Claims, 9 Drawing Sheets

(56) References Cited

U.S. PATENT DOCUMENTS

| | | | |
|---|---|---|---|
| 2007/0270879 A1* | 11/2007 | Isaza | A61B 17/1742 |
| | | | 606/104 |
| 2008/0154377 A1 | 6/2008 | Voellmicke | |
| 2009/0216238 A1* | 8/2009 | Stark | A61F 2/30988 |
| | | | 606/96 |
| 2013/0035723 A1 | 2/2013 | Donner | |
| 2014/0277485 A1* | 9/2014 | Johnson | A61F 2/4455 |
| | | | 623/17.16 |
| 2015/0051704 A1* | 2/2015 | Duffield | A61F 2/442 |
| | | | 623/17.16 |
| 2017/0007409 A1 | 1/2017 | Mauldin | |

* cited by examiner

IMPLANTS AND IMPLANTATION TECHNIQUES FOR SACROILIAC JOINT FUSION

CROSS-REFERENCE TO RELATED APPLICATION

The Applicant claims the benefit, under 35 U.S.C. § 119(e), of U.S. Provisional Patent Application No. 62/769, 489 filed Nov. 19, 2018, and entitled "Implant and Implantation Technique for Sacroiliac Joint Fusion." The entire content of this provisional application is incorporated herein by this reference.

TECHNICAL FIELD OF THE INVENTION

The invention relates to devices and techniques for facilitating the fusion of the sacroiliac joint (the "SI joint"). More particularly, the invention relates to devices and techniques for securing suitable bone fusion material in the SI joint and stabilizing the joint to facilitate fusion between the sacrum and ilium.

BACKGROUND OF THE INVENTION

The SI joint is composed of the ilium articulation to the sacrum to form a diarthrodial joint with 2 to 4 mm of multi planar motion. The iliac convex side of the SI joint is covered with fibrocartilage while the sacral side of the SI joint is concave and covered in articular cartilage. The SI joint can become a pain generator in an individual due to degenerative change in the joint and due to changes occasioned by injury. Sacroiliac pathology may be diagnosed with maneuvers that increase pressure or load to the SI joint to elicit buttock and low lateral sacral pain which is characteristic of sacroiliac pain. X-rays, MRI, and CT scan may also aid in the diagnosis of sacroiliac pathology.

Sacroiliac joint pain is commonly treated initially with anti-inflammatory injections, and/or radio frequency ablation. When these treatments fail, fusion of the joint is indicated. Prior methods of sacroiliac fusion include screw or other fixation devices placed from a lateral or oblique approach directly across the joint. Some of these techniques involve placing bone inductive and conductive material such as allograft, autogenous bone, stem cells, bone marrow aspiration, or other bone fusion materials such as a bone morphogenic protein in an effort to encourage bone growth across the SI joint to effect fusion of the joint. These techniques of placing bone inductive and conductive materials in connection with screw or other fixation devices directly across the SI joint commonly fail to place sufficient material to facilitate fusion of the joint via inter articular surface bone growth in a desirable time frame.

U.S. Pat. No. 8,979,928 discloses an implant that is inserted into the articular region of the SI joint to facilitate fusion of the joint. Apertures are provided in the implant shown in this patent for receiving biologically active agents and biocompatible materials to encourage bone growth across the SI joint. However, the structure of the implants shown in U.S. Pat. No. 8,979,928 allows little area for such materials relative to the overall area of the implant in the SI joint articular region.

SUMMARY OF THE INVENTION

It is an object of the invention to provide an implant for facilitating SI joint fusion via bone growth between the sacrum and ilium across the articular region of the SI joint. Implants according to the aspects of the invention provide relatively large areas for bone growth across the SI joint while maintaining sufficient structural integrity to withstand the forces required for implantation. Additionally, implants according to the present invention may be specifically designed to the details of the SI joint anatomy.

An implant according to a first aspect of the invention includes an implant structure formed from an elongated base member, an elongated first side member, and an elongated second side member. The base member has a base member longitudinal axis extending parallel to an implant width axis and perpendicular to an implant longitudinal axis. The base member longitudinal axis defines a base of a triangle in an implant plane defined by the implant width axis and implant longitudinal axis, while the first side member and second side member each extend along a respective longitudinal axis which defines a respective lateral side of the triangle. An implant according to this first aspect of the invention further includes an internal support structure extending in the implant plane from the base member to each of the first side member and the second side member. Three or more fusion passages are defined in an area between the base member, first side member, and second side member. Each fusion passage extends along a thickness axis perpendicular to the implant plane and defines a respective open area through the implant.

Although the triangular shaped arrangement of this first aspect of the invention is a preferred form of the implant because it generally provides a good match to the details of the SI joint structure for most patients, the present invention is not limited to this triangular shaped arrangement. Thus an implant according to a second aspect of the invention may take other shapes. An implant according to this second aspect of the invention includes a base structure and an insertion end structure spaced apart from the base structure along an implant longitudinal axis. An elongated first side member extends along a first side longitudinal axis and defines a first lateral side of the implant, while an elongated second side member extends along a second side longitudinal axis and defines a second lateral side of the implant. These first and second lateral side of the implant are spaced apart along an implant width axis which lies perpendicular to the implant longitudinal axis and together with the implant longitudinal axis defines an implant plane. An implant according to this second aspect of the invention further includes an internal support structure extending in the implant plane from the base structure to the insertion end structure. Two or more fusion passages are defined in an area between the first side member, second side member, base structure, and insertion end structure, each fusion passage extending along a thickness axis perpendicular to the implant plane and defining a respective open area through the implant.

An implant according to either the first or second aspect of the invention may be formed from one or more biologically compatible materials and may be implanted in an implantation position within an SI joint generally with the thickness axis of the implant extending transversely across the joint from the sacrum to the ilium. In this implantation position, the implant stabilizes the SI joint against articulation while the areas defined by the fusion passages provide areas for bone growth from the sacrum to the ilium across the SI joint to effect or enhance fusion of the joint. The configuration of the implant base and side members (or base structure, insertion end structure and side members) together with the internal support structure allows the open areas defined by the fusion passages to be maximized to thereby maximize the area of bone for fusion of the SI joint. In particular, the configuration of implants according to the first and second aspects of the invention provides a structure that may withstand the forces applied in the course of implantation while maximizing the area across the implant for fusion of the SI joint.

The areas defined by the fusion passages may be filled with bone fusion material which may encourage bone growth across the SI joint and thus fusion of the joint. As used in this disclosure and the accompanying claims, "bone fusion material" comprises one or more bone inductive materials or one or more bone conductive materials, or combinations of the two types of materials. These materials include allograft, autogenous bone, stem cells, bone narrow aspiration, bone morphogenic protein or any other material now known or developed in the future to help induce or support, or both induce and support, bone growth from one bone surface to another. "Biologically compatible material" as used in this disclosure and the accompanying claims comprises any material suitable for implantation in an SI joint. This includes various types of stainless steel and various types of plastic, and any other material now known or that may be developed in the future for use in forming implants which may be implanted in the SI joint.

In some implementations of an implant according to the first or second aspect of the invention, the internal support structure includes two or more beams extending transverse to the implant width axis in the implant plane. These two or more beams divide the area between the first side member, second side member, and base member into the fusion passages. The two or more beams may include a first lateral beam and a second lateral beam. In such implementations according to the first aspect of the invention, the first lateral beam extends along a first lateral beam longitudinal axis from a first lateral beam base end connected to the base member to a first lateral beam forward end connected to the first side member. The second lateral beam extends along a second lateral beam longitudinal axis from a second lateral beam base end connected to the base member to a second lateral beam forward end connected to the second side member. The first and second lateral beams may converge in a direction along the implant longitudinal axis from a forward end of the implant to the base member. This beam arrangement and other beam arrangements which may be employed in the internal support structure of an implant according to the first and second aspects of the invention provide support for the first and second side members of the implant and help those members withstand the forces which may be encountered during implantation.

The first side member, second side member, and other elements of the implant according to the first or second aspects of the invention may define a first joint contact surface on one side of the implant plane and a second joint face contact surface on an opposite side of the implant plane. In some implementations of an implant according to this aspect of the invention, the two joint face contact surfaces extend at an angle of between approximately 5 and 15 degrees, and more preferably between approximately 8 and 12 degrees to each other in a direction between the base and forward end of the implant along the implant longitudinal axis, that is between the base member and forward end of an implant according to the first aspect of the invention and between the base structure and insert end structure of the second aspect of the invention.

Implants according to either the first or second aspect of the invention may also include a retention feature formed on each of the joint face contact surfaces. Such retention features may help retain the implant in the implanted position once it has been placed in that position by the surgeon. These retention features may comprise a number of ridges spaced apart along the implant longitudinal axis and extending parallel to the width axis. Once the implant is impacted into the implanted position as will be discussed below, the ridges serve to catch on the prepared SI joint surface and help prevent the implant from sliding out of the desired implanted position along the implant longitudinal axis.

In some implementations of an implant according to the first aspect of the invention the elongated base member, elongated first side member, and elongated second side member may meet so that the members form a triangular shape in the implant plane. However, the present invention is not limited to such an arrangement. Other implementations may include a portion of one or more of the elongated first or second side members adjacent to the elongated base member that extend (for example) parallel to the implant longitudinal axis. In these implementations, the elongated base member may have a length dimension that is less than a dimension defined between a first point at which the first side longitudinal axis intersects the base member longitudinal axis in the implant plane and a second point at which the second side longitudinal axis intersects the base member longitudinal axis in the implant plane.

Implants according to either the first or second aspect of the invention may also be adapted to receive a locking element once the implant is placed in the implanted position in the SI joint. Such a locking element may be configured to help secure the implant in the implanted position. A suitable connector arrangement may be used to connect the locking element to the base member (or base structure in the second aspect of the invention) in a locking position. The connector arrangement may include at least one fastener opening through the locking element and adapted to align with a threaded opening in the implant base member or base structure. In this aligned position a suitable threaded fastener may be placed in the fastener opening and driven into the threaded opening to connect the locking element to the implant. The base member (or base structure in the second aspect of the invention) may include an elongated channel and the locking element may include a projection configured to be received in the channel to help align the locking element in the desired position. Once connected to the implant, a fixation device such as a suitable bone screw may be driven into a receiver opening in the locking element and into adjacent bone of the sacrum or ilium to help secure the implant in the desired implanted position. A locking element may include two receiver openings, one aligned to place a fixation device in the sacrum and one to place a fixation device in the ilium.

The invention also encompasses a method for effecting a fusion of the SI joint. This aspect of the invention includes forming a sacral side implant receiving surface in the sacral side of the SI joint and forming an iliac side implant receiving surface in the iliac side of the SI joint opposite the sacral side implant receiving surface. These two implant receiving surfaces define an SI joint implant receiving volume for receiving an SI joint implant according to the first aspect of the invention as described above. A method according to this aspect of the invention then includes fixing the SI joint implant in the SI joint implant receiving volume in an implantation position in which the fusion passages extend transversely across the SI joint. As will be described below in connection with the drawings, fixing the implant in the implanted position may include driving the implant into the implant receiving volume with a suitable insertion or impacting tool. Fixing the implant in the implanted position may also include removing the insertion tool from the implant, attaching the locking element to the implant as described above, and then placing at least one surgical fastener through the receiver opening of the locking element so as to extend into the sacrum or ilium.

These and other advantages and features of the invention will be apparent from the following description of representative embodiments, considered along with the accompanying drawings.

DESCRIPTION OF REPRESENTATIVE EMBODIMENTS

Figure 12:
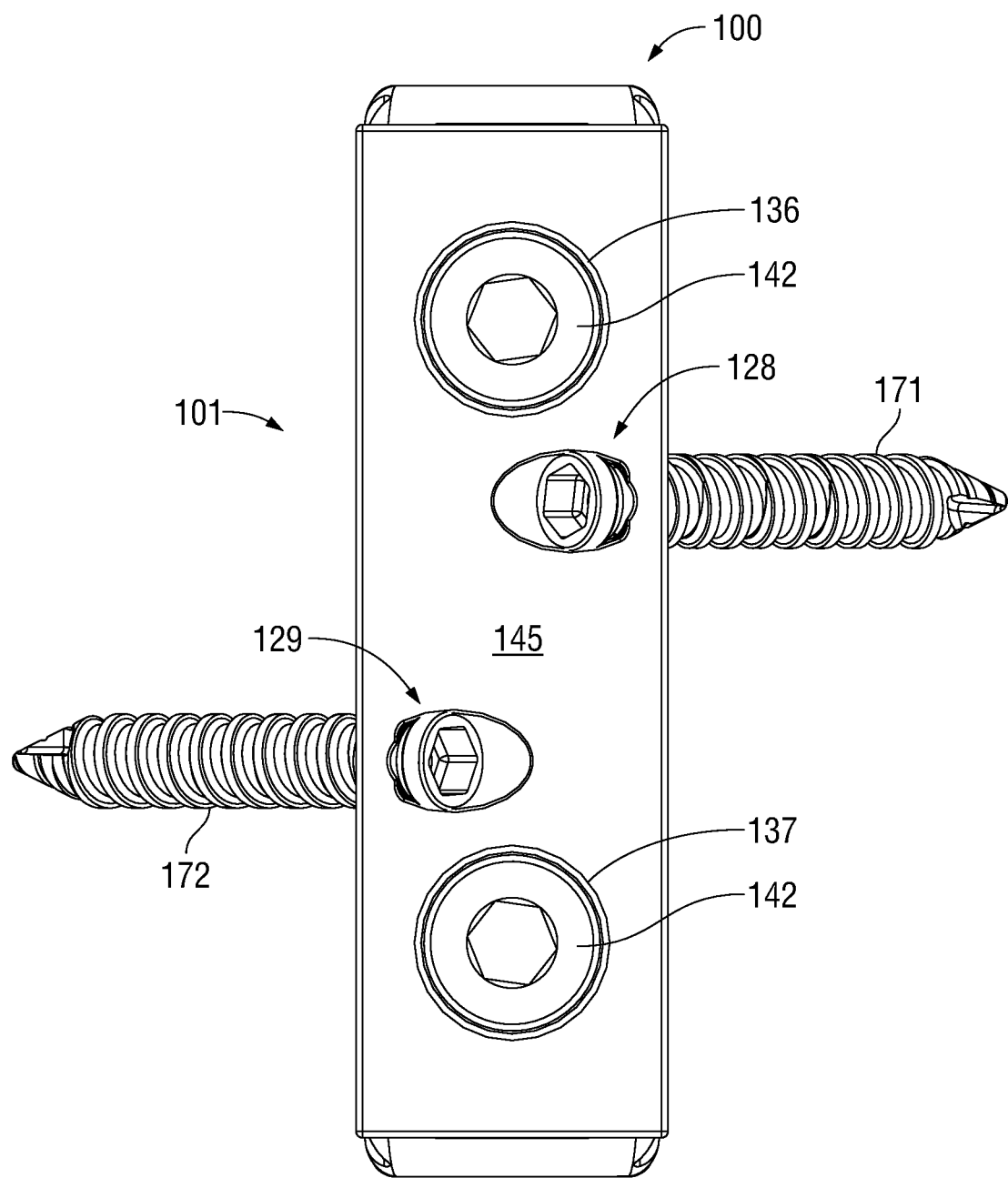
FIG. 12 is a view of the implant in generally the same orientation as shown in 9-11, but showing fasteners as they would be installed in locking element 101 to help fix implant 100 in the implanted position.
Figure 13:
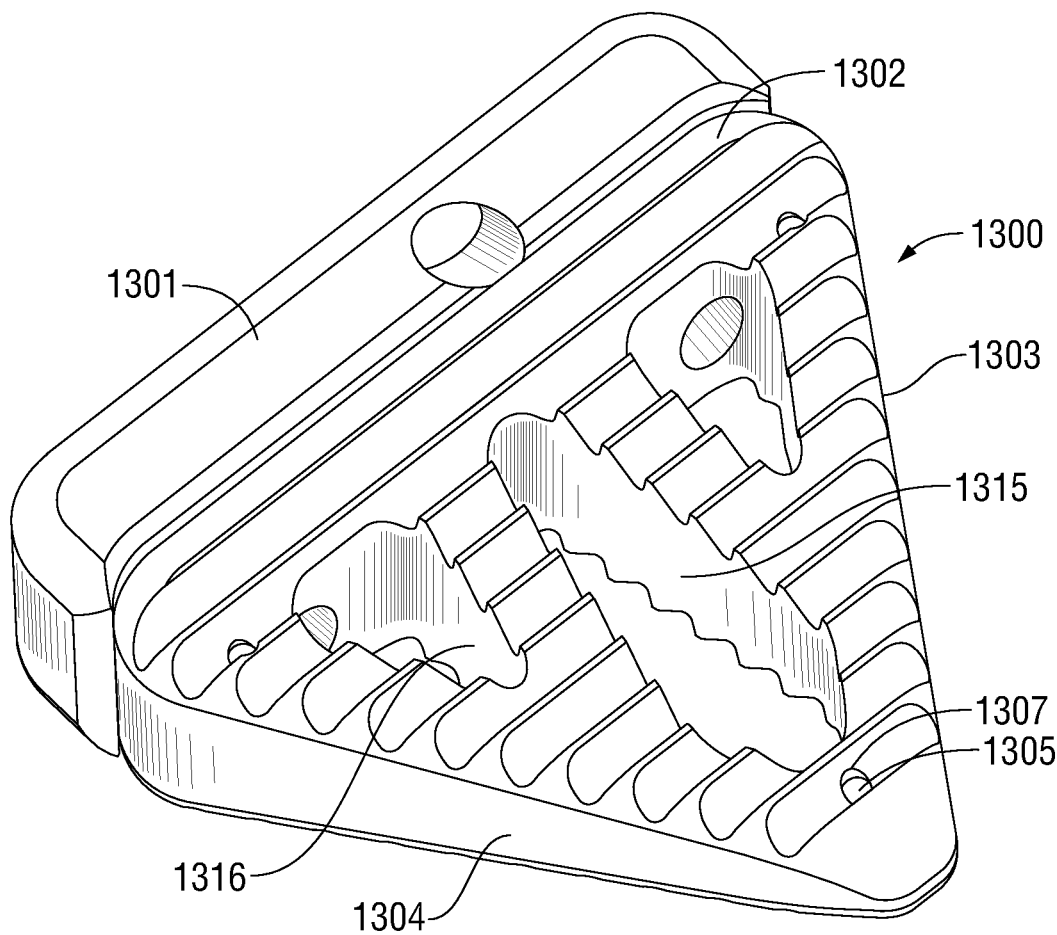
FIG. 13 is a front left perspective view of an alternate implant embodying the principles of the present invention together with an attached locking element.
Figure 14:
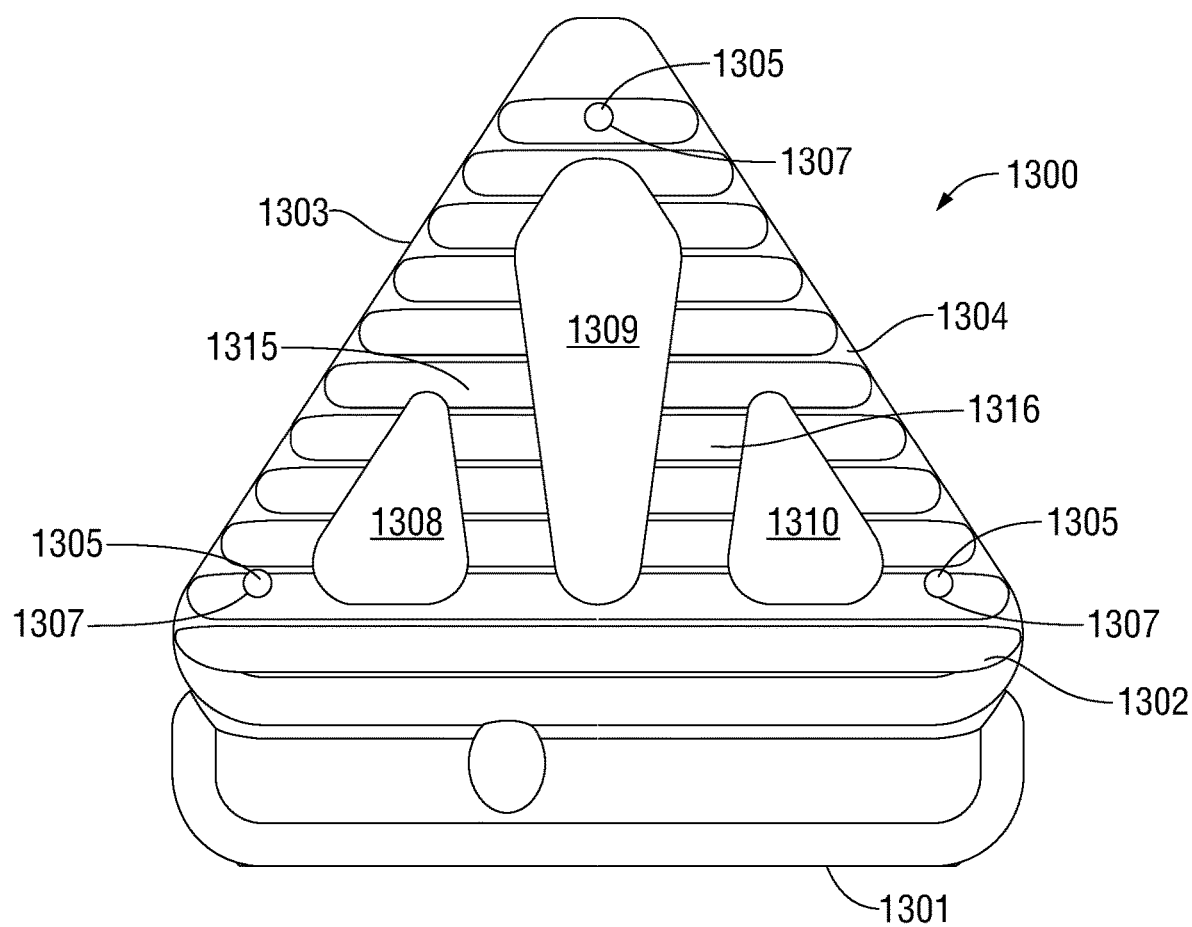
FIG. 14 is a top plan view of the implant and locking element shown in FIG. 13.
Figure 15:
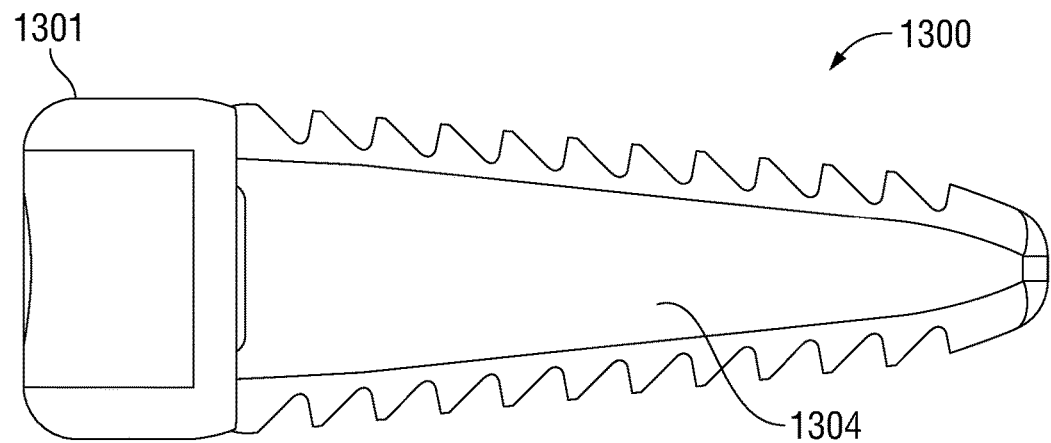
FIG. 15 is a side view of the implant and locking element shown in FIG. 13.

In the following, FIGS. 1-6 will be referenced to describe an example SI joint implant 100 embodying principles of the present invention and a locking element 101 which may be used with the implant 100. FIGS. 7-12 will be referenced in connection with describing procedures by which implant 100 may be implanted in an SI joint, and in connection with describing the installation and use of locking element 101. FIGS. 13-15 will be referenced to describe another example SI joint implant and locking element embodying the principles of the present invention.

Figure 1:
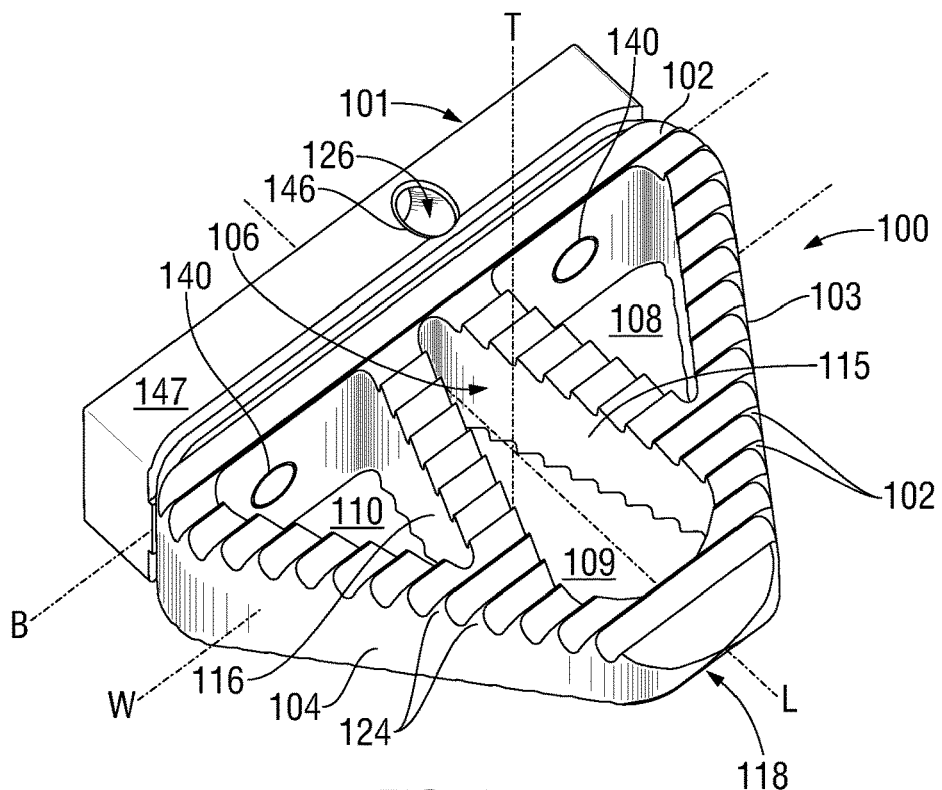
FIG. 1 is front left perspective view of an implant embodying the principles of the present invention together with an attached locking element.
Figure 2:
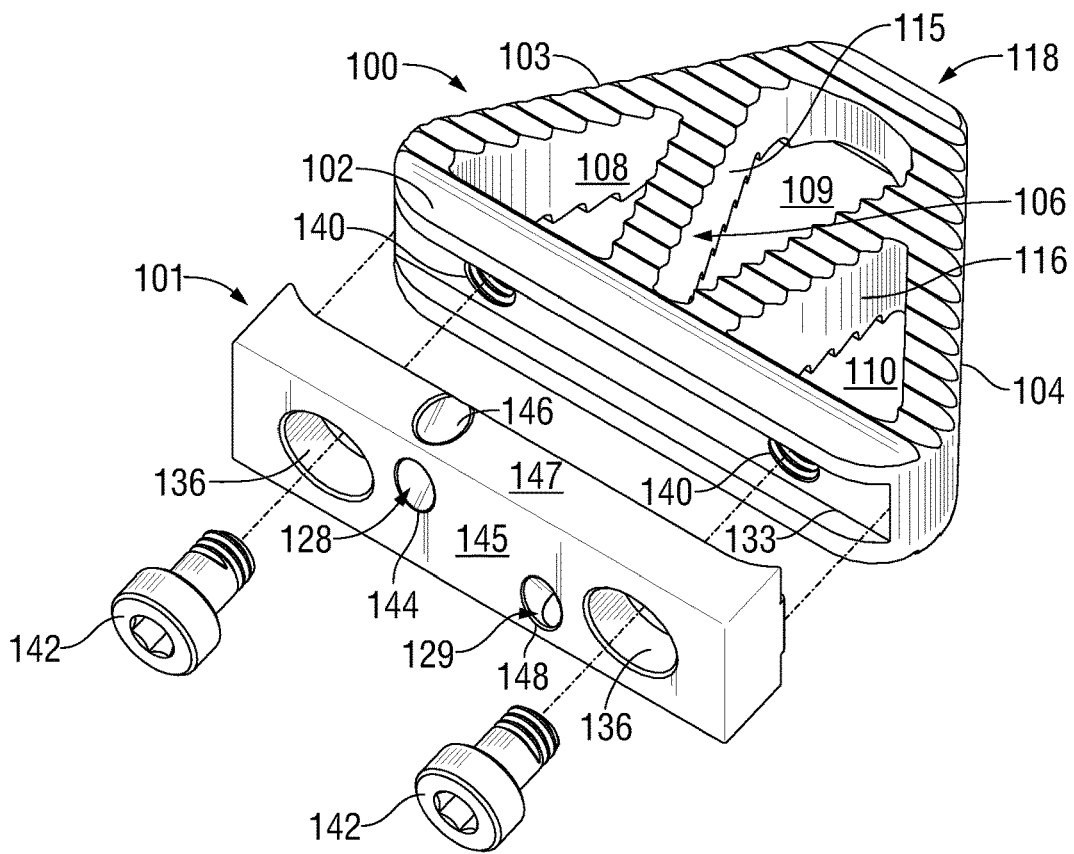
FIG. 2 is an exploded rear left perspective view of the implant and locking element shown in FIG. 1.
Figure 3:
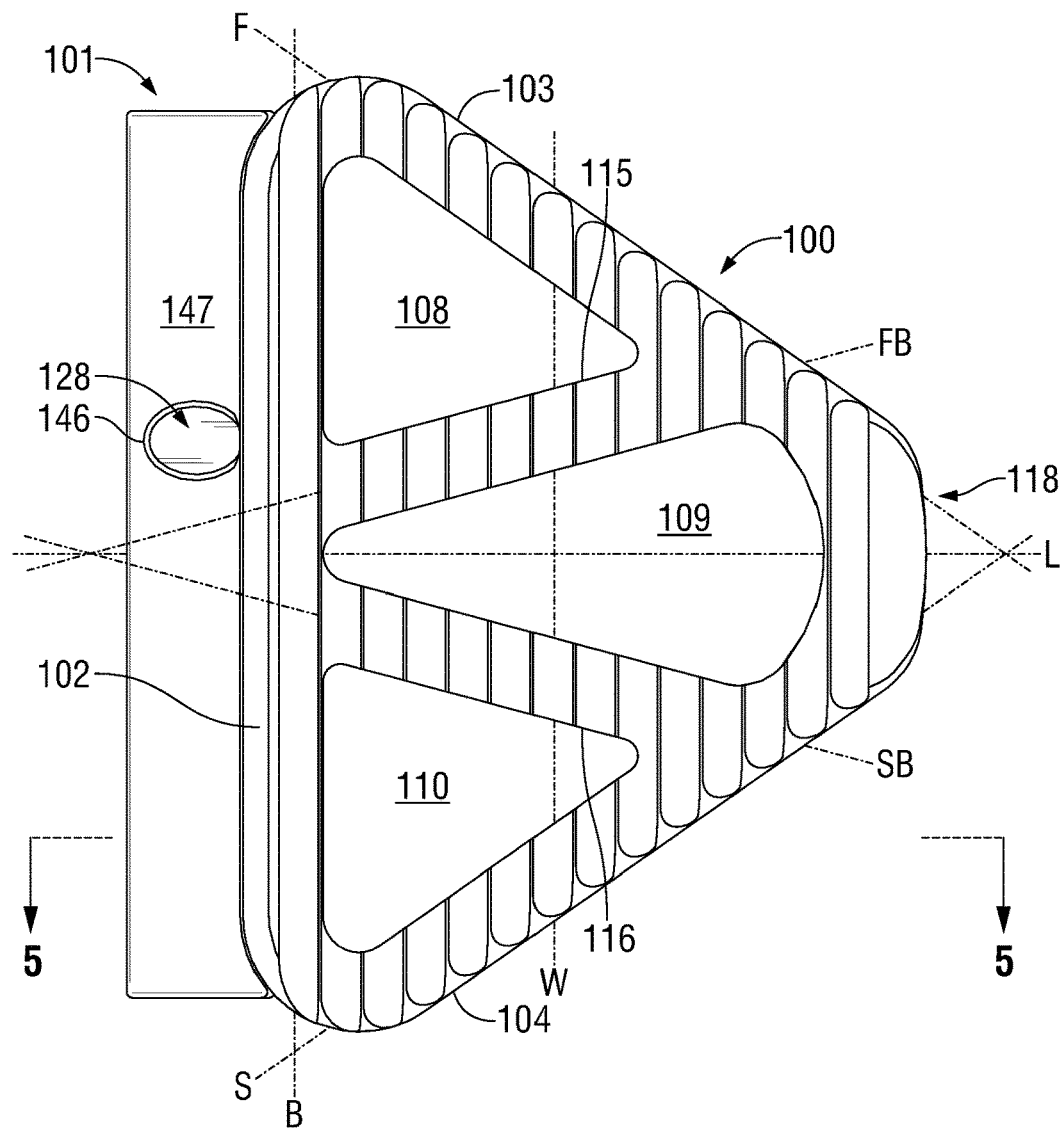
FIG. 3 is a top plan view of the implant and locking element shown in FIG. 1.

Referring to FIGS. 1-4, the example SI joint implant 100 includes an elongated base member 102, an elongated first side member 103, and an elongated second side member 104. Implant 100 also includes an internal support structure shown generally at reference number 106 in the figures. As shown in FIG. 1, base member 102 has a longitudinal axis B extending parallel to an implant width axis W and perpendicular to an implant longitudinal axis L. These axes W and L define an implant plane, with a thickness axis T of the implant extending perpendicular to the implant plane. As shown in the plan view of FIG. 3, first side member 103 extends along a first side longitudinal axis F while second side member 104 extends along a second side longitudinal axis S. FIG. 3 also shows that the longitudinal axis B of base member 102 forms a base of a triangle in the implant plane while first side longitudinal axis F and second side longitudinal axis S form the two lateral sides of the triangle. In this particular example implant 100, longitudinal axis B forms the base of an isosceles triangle with the side longitudinal axes F and S forming the sides of the isosceles triangle.

Implant 100 also includes a number of fusion passages defined in the area between base member 102, first side member 103, and second side member 104. This particular example implant, includes three fusion passages 108, 109, and 110. Each of these fusion passages 108, 109, and 110 extend along the thickness axis T and define a respective open area through implant 100 in the direction of thickness axis T. As will be described further below, the fusion passages 108, 109, and 110 provide areas for bone growth across implant 100 when properly positioned in an SI joint to facilitate fusion of the joint.

Internal support structure 106 in example implant 100 includes two beams extending transverse to implant width the axis W. In particular, implant 100 includes a first lateral beam 115 extending along a first lateral beam longitudinal axis FB (FIG. 3), and a second lateral beam 116 extending along a second lateral beam longitudinal axis SB (FIG. 3). First lateral beam 115 has a base end connected to base member 102 and a forward end connected to first side member 103. Second lateral beam 116 includes a base end connected to base member 102 and a forward end connected to second side member 104. In this particular embodiment, first lateral beam 115 and second lateral beam 116 converge in a direction along the implant longitudinal axis L from a forward end of the implant shown generally at 118 to base member 102. This convergence is particularly apparent in the plan view of FIG. 3. Regardless of the particular arrangement of beams making up internal support structure 106, such as beams 115 and 116 in the illustrated embodiment, these members divide the area of the implant between base member 102, first side member 103, and second side member 104 to define the fusion passages, in this example, passages 108, 109, and 110.

The function of internal support structure 106, which in this example is made of up of lateral beams 115 and 116, is to provide support in the implant plane for the first and second sides members, 103 and 104 respectively. Support is desirable particularly for resisting forces applied to these side members in a direction along the longitudinal axis L from implant forward end 118 to the base member 102. Forces in this direction are encountered in the course of placing the implant in an implanted position in an SI joint as will be described further below in connection with FIGS. 7-12. Numerous other beam arrangements may be used to provide suitable support for side members 103 and 104 against forces applied to the implant in the course of implantation. For example, rather than two discrete beams, the internal support structure may include an arrangement of elements forming generally a Y shape with an elongated member extending from a midpoint of base member 102 to form the bottom part of the Y shape, and then two diverging elements, each extending to a respective side member and forming the upper part of the Y shape. Additional alternative internal support structures may include elements defined between a number of circular or other shaped openings in the area of the implant defined between the base member and side members. These circular or other shaped openings in alternative embodiments define the fusion passages in those embodiments. Because the beams or other structures making up internal support structure 106 provide support for the first and second side members 103 and 104, the fusion passages defined through the support structure will typically include at least three such passages. However, it is possible for an internal support structure to be configured within the scope of the invention to include only fusion passages or perhaps only one fusion passage. In any case the area of the fusion passage or passages according to the present invention is preferably maximized to provide the maximum area for bone growth across the implant when properly positioned in an SI joint.

In the illustrated example implant 100, first side member 103, second side member 104, base member 102, and internal support structure 106 define joint contact surfaces on either side of the implant plane. As shown in the side view of FIG. 4, a first joint contact surface extends along a line C1 on a first side of the implant plane (the implant plane extending perpendicular to the plane of the drawing page in this view along longitudinal axis L). A second joint face contact surface extends along line C2 on the opposite side of the implant plane in FIG. 4. In this embodiment, these two joint face contact surfaces extend at an angle A between approximately 5 and approximately 15 degrees, and more preferably between approximately 8 and approximately 12 degrees to each other in a direction along the implant longitudinal axis L from forward end 118 to base member 102. As will be described further below particularly in describing the implantation process in connection with FIGS. 7-11, each of these two joint face contact surfaces faces a prepared surface in the articular region of the SI joint when the implant is placed in an implanted position in the SI joint. In particular, one joint face contact surface will face a prepared surface in the sacrum while the other joint face contact surface faces a prepared surface in the ilium.

Figure 4:
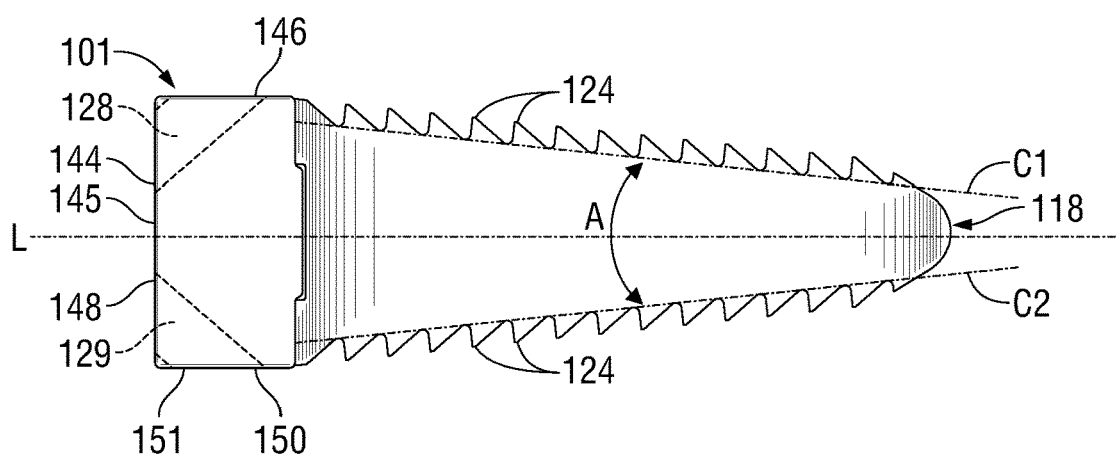
FIG. 4 is a left side view of the implant and locking element shown in FIG. 1.

In order to help facilitate retention of the implant in the implanted position, example implant 100 includes a respective retention feature formed on each joint face contact surface. The retention feature in each case comprises a number of ridges or teeth 124 spaced apart along implant longitudinal axis L and extending parallel to width axis W. As best shown in FIG. 4, ridges 124 in the illustrated example implant 100 are angled rearwardly and in position to bite into the prepared bone surface on each side of the implant plane. As will be discussed below in connection with the implantation method, this contact helps prevent the implant from sliding rearwardly out of the desired implanted position.

Figure 5:
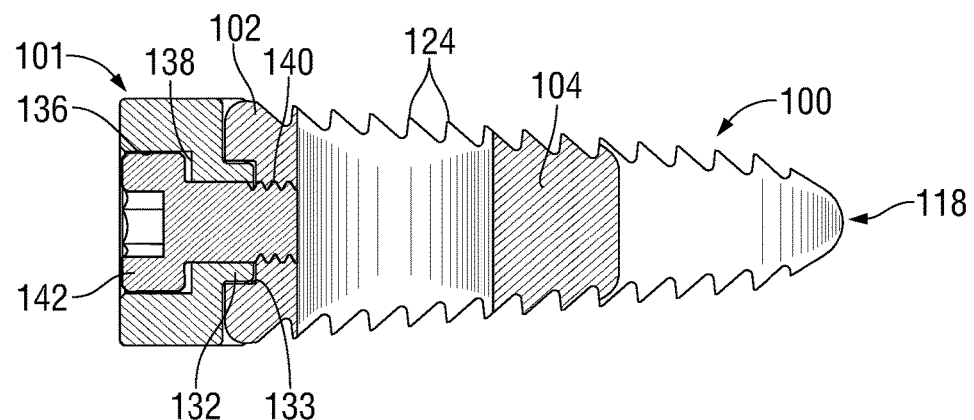
FIG. 5 is a section view taken along line 5-5 in FIG. 4.
Figure 6:
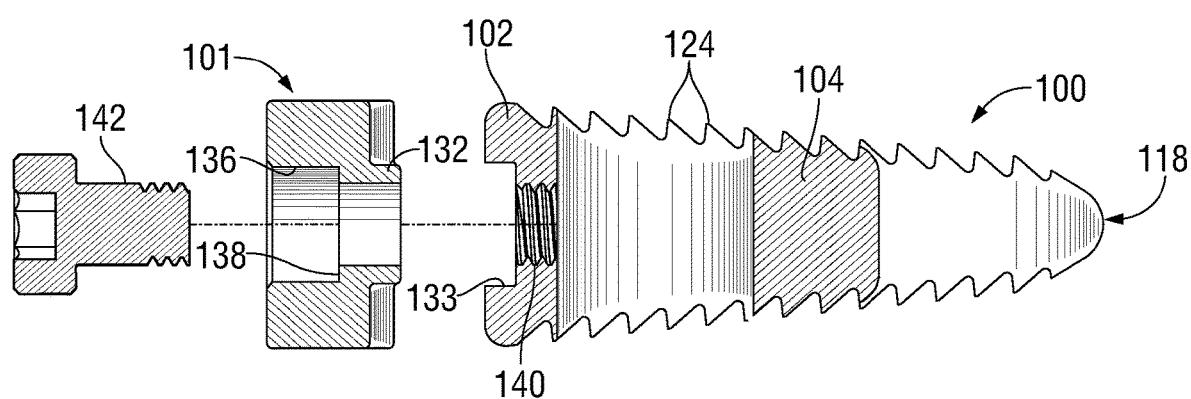
FIG. 6 is an exploded section view taken along line 5-5 in FIG. 4.
Figure 7:
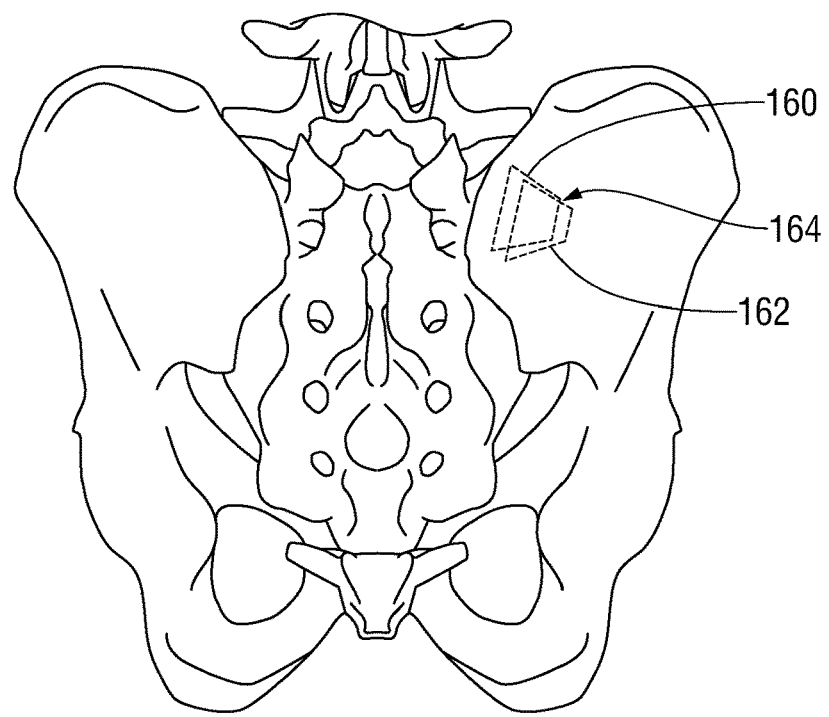
FIG. 7 is a posterior view of the sacrum and ilium with the implant receiving surfaces formed opposite each other in the right SI joint.

As will be described further below in connection with the implantation method, locking element 101 provides an additional feature that may be used with implant 100 to help secure the implant in the desired implanted position. The illustrated locking element 101 includes two fixation device receivers 128 and 129 shown best by the phantom lines in FIG. 4, and a connector arrangement for connecting the locking element to base member 102. In this connected position a longitudinal axis of locking element 101 extends parallel to the longitudinal axis B of base member 102. As shown in FIGS. 5 and 6, the example locking element 101 includes a projection 132 configured to be received in a channel 133 formed along base member 102 when the locking element is properly connected to base member 102. Locking element 101 also includes two fastener openings 136 each with a fastener shoulder 138. Each fastener opening 136 is adapted to align with a respective threaded opening 140 of base member 102 when locking element 101 is in the properly aligned position. In this position a respective fastener 142 may be inserted into each fastener opening 136 and threaded in to the respective threaded opening 140 to the position shown particularly in the section view of FIG. 5 to connect locking element 101 to implant 100.

It will be appreciated particularly from FIG. 4 that when the locking element 101 is connected to base member 102 in the proper locking position, each fixation device receiver 128 and 129 formed in the locking element extends at an acute angle to implant longitudinal axis L in the direction from base member 102 to forward end 118 of the implant. Fixation device receiver 128 comprises a cylindrical bore extending along that acute angle from an opening 144 in a top surface 145 of locking element 101 to an opening 146 in a first side surface 147 of the locking element. Fixation device receiver 129 comprises a cylindrical bore extending at the acute angle on the opposite side of locking element 101 from an opening 148 in top surface 145 to an opening 150 in a second side surface 151 of the locking element. In these positions, fixation device receivers 128 and 129 are each in position to receive a device such as a suitable bone screw to secure the locking element 101 and connected implant 100 in the implanted position as will be described further below.

While the example implant 100 shown in the drawings has a generally triangular shape in the implant plane, implants within the scope of the present invention need not have such a triangular shape. For example, even where the implant includes a base member such as base member 102, the side members of the implant may include portions that extend parallel to each other where they meet the base member. Still other embodiments of an implant according to them present invention may include an oval or circular shape in the implant plane, or other polygonal shape, or even an irregular shape in the implant plane.

Methods of effecting SI joint fusion according to the present invention may be described with reference to the example implant 100 shown in FIGS. 1-6 and with reference to the anatomical views of FIGS. 7-12. Although the following description will reference example implant 100, it will be appreciated that the processes apply to any implant within the scope of the present invention.

Generally, methods according to the invention include forming implant receiving surfaces in the sacral side and iliac side of the SI joint in order to form an implant receiving volume between the sacrum and ilium for receiving implant 100. The method then includes fixing implant 100 in the implant receiving volume in an orientation in which the fusion passages extend transversely across the SI joint in position to facilitate bone growth across the prepared surfaces of the sacrum and ilium to thereby fuse the joint. Implants placed in this fashion not only stabilize the SI joint against articulation so as to facilitate fusion, but also provide a large area (the implant fusion passages) for bone growth to effect fusion.

When implant 100 is implanted as a separate procedure, implantation requires first providing suitable access to the SI joint which is to be fused. The procedure may include first palpating and marking the super iliac crest, and making an oblique incision through the skin, taking the dissection through the subcutaneous tissue. The posterior superior iliac crest may then be palpated and the dissection carried down to the sacroiliac joint referencing the medial table of the posterior superior ilium. The concave depression on the iliac side of the SI joint (referenced here as the "posterior iliac fossa") may then be palpated and developed with further dissection. From this point electrocautery may be employed to take down a portion of the iliolumbar ligament to expose the short dorsal sacroiliac ligaments which may also be taken down with electrocautery. The sacroiliac interosseous ligaments are then encountered and taken down with electrocautery.

Figure 8:
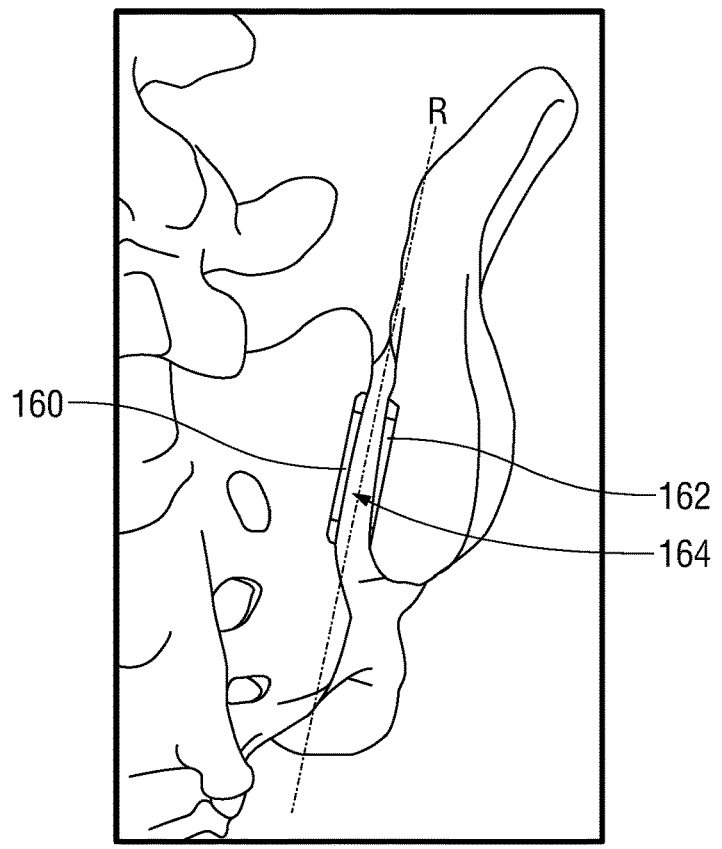
FIG. 8 is a view of a portion of the sacrum and ilium rotated with respect to the view of FIG. 7 so that the longitudinal axis of the implant receiving volume extends generally perpendicular to the plane of the drawing.

After the process described in the preceding paragraph, the SI joint is exposed and the procedure continues with forming the implant receiving surfaces. To form these surfaces the SI joint may be entered with curettes for curettaging the fibrocartilage on the iliac side of the joint until the decorticated and punctate bleeding is encountered. The sacral side may also be curettaged with curettes as well also until punctate bleeding is encountered. The dissection is taken deeply into the SI joint in this manner of dissection until an ample space is created. Cage rasps may then be used to form and even the curettaged surfaces of the joint to produce the sacral side implant receiving surface shown at 160 in FIGS. 7 and 8 and the iliac side implant receiving surface shown at 162, and to size the implant receiving volume 164 (comprising the space between the two surfaces) in preparation for implant trials. Once the correct implant size is selected, the procedure includes connecting the selected implant 100 to an inserter (not shown) with which the implant may be impacted into the implant receiving volume 164. The inserter may be connected to implant 100 in any suitable fashion, such as by suitable fasteners to threaded openings 140 in base member 102 of the implant. Once implant 100 is connected to the inserter, the implant is aligned with implant receiving volume 164 so that the implant plane coincides generally with a plane of the implant receiving volume. This plane of implant receiving volume 164 is indicated in FIG. 8 (and FIG. 10) as line R where the plane perpendicularly intersects the plane of the drawing sheet. With implant 100 properly aligned the inserter may be impacted to drive implant 100 into implant receiving volume 164 to the implanted position shown in FIGS. 9-11. Once implant 100 is in the desired implanted position, the inserter is detached from implant 100 and removed, leaving the implant in the implanted position. In this implanted position the fusion passages of implant 100 (passages 108, 109, and 110 shown in FIGS. 1-3) will extend transversely across the SI joint in position to allow bone growth between the prepared surfaces 160 and 162 of the joint to effect the desired fusion of the joint. Preferably the fusion passages 108, 109, and 110 of implant 100 are filled with one or more fusion materials prior to insertion and impaction into the implant receiving volume. When implant 100 is placed in the implanted position shown in FIGS. 9-11, the bone fusion material encourages and/or supports bone growth between surfaces 160 and 162 to effect the fusion of the SI joint.

Figure 9:
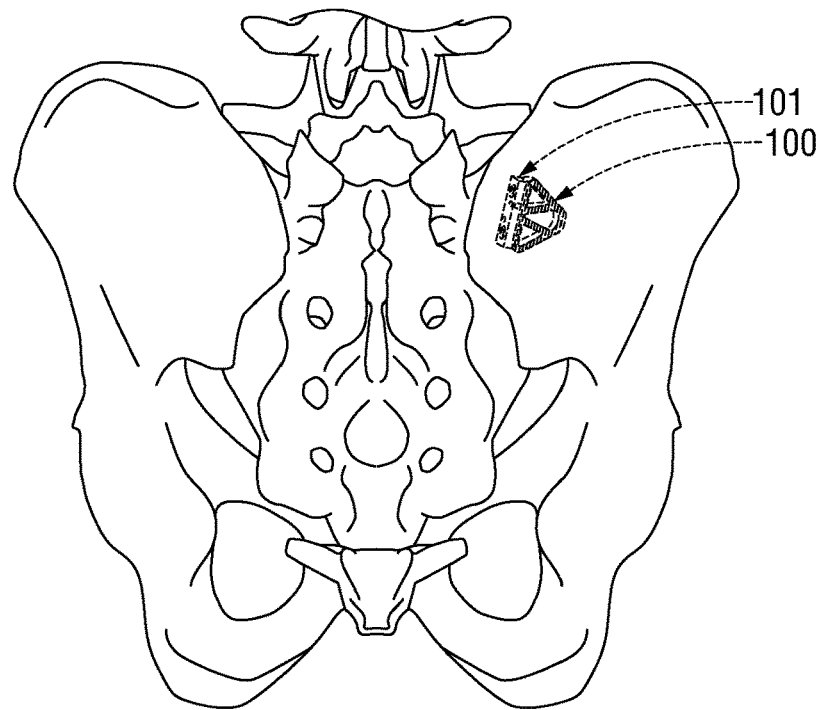
FIG. 9 is a view similar to FIG. 7 but showing the implant of FIGS. 1-6 fixed in the implanted position within the SI joint.
Figure 10:
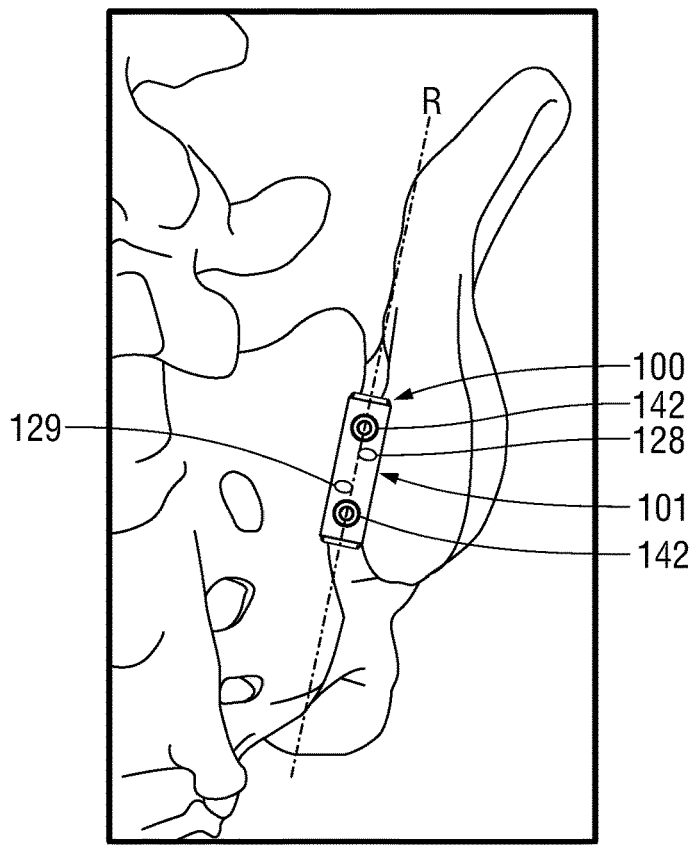
FIG. 10 is a view similar to FIG. 8 but showing the implant of FIGS. 1-6 fixed in the implanted position within the SI joint.
Figure 11:
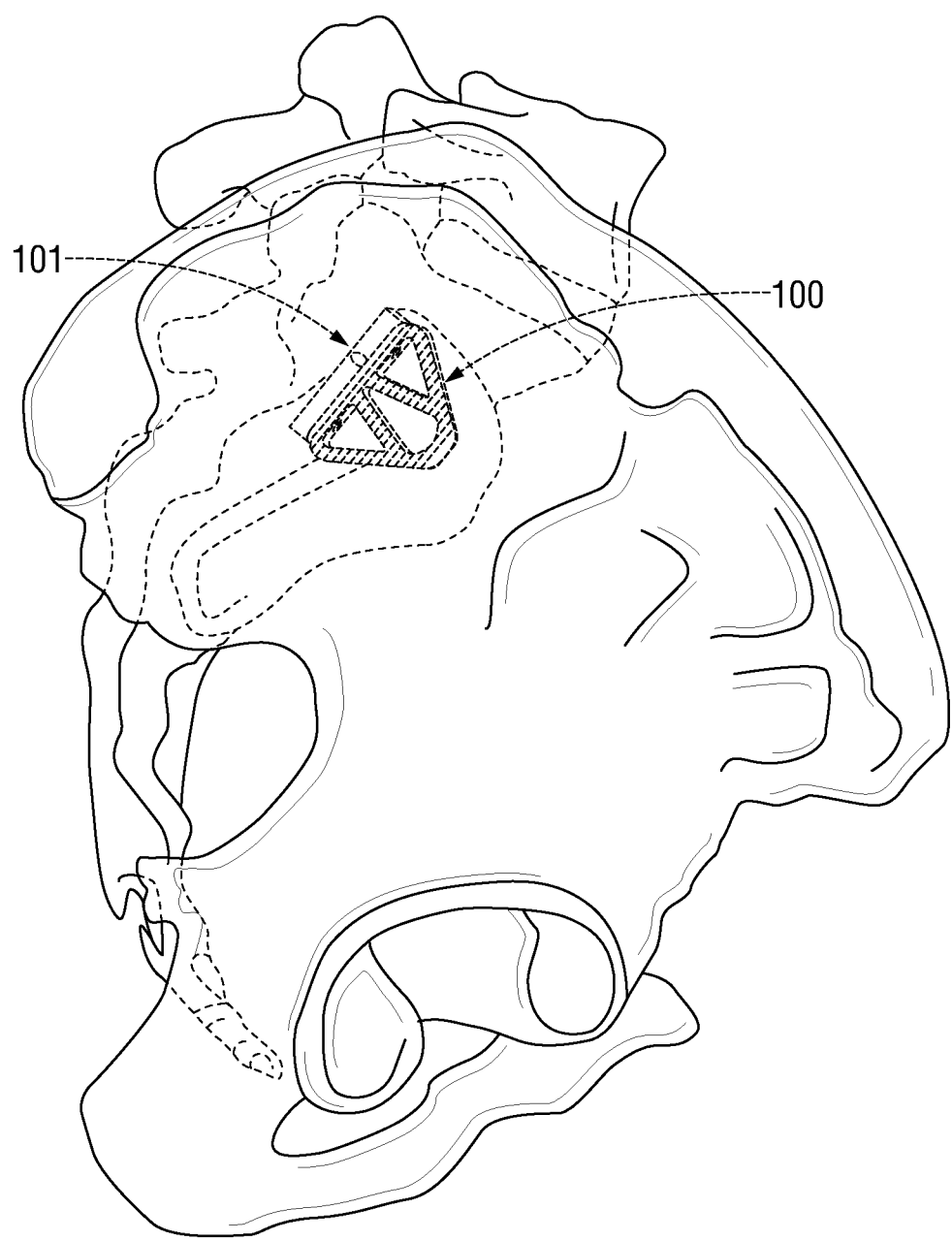
FIG. 11 is a right side view of the sacrum, ilium, and implant in the implanted position shown in FIGS. 9 and 10.

A proper tight fit between implant 100 and implant receiving surfaces 160 and 162 and the impaction into SI joint implant receiving volume 164, together with the ridges or teeth 124 provided on implant 100 may be sufficient for ensuring that the implant remains fixed in the implanted position shown in FIGS. 9-11. It may be desirable, however, to use locking element 101 to ensure that implant 100 is fixed in implant receiving volume 164. Where locking element 101 is employed, it may be connected to implant 100 once the implant is placed in the desired implanted position and the inserter removed. It will be noted that in the orientation of the view in FIG. 10 (and FIG. 12) locking element 101 mostly obscures implant 100 with only a small portion of implant 100 visible at either end of locking element 101. The connection between implant 100 and locking element 101 is made using fasteners 142 shown in FIGS. 1, 2, 5, 6, 10 and 12. Once locking element 101 is connected to implant 100, suitable fixation devices such as bone screws (not shown in FIG. 9-11) may be placed through one or both fixation device receivers 128 and 129. The angle of the receivers 128 and 129 allows the bone screw or other fixation device to penetrate into the adjacent bone structure, sacrum or ilium, on that side of implant 100 to further fix the implant in the implanted position. The larger scale view of FIG. 12 shows fixation devices comprising bone screws 171 and 172 in receivers 128 and 129, respectively. Bone screws 171 and 172 are each shown in an installed position in the respective receiver, and may comprise any type of bone screw suitable for use in bone. Preferably, each bone screw 171 and 172 may have the same configuration as screws used in other procedures involving the ilium, such as hip joint replacement for example. Although implant 100 and locking element 101 are shown separately from the sacrum and ilium in FIG. 12, the orientation of the implant 100 is essentially the same as that shown in FIG. 11. Thus it will be appreciated from FIGS. 11 and 12 that bone screw 171 would extend into the ilium when placed in the installed position in receiver 128 with implant 100 in the implanted position shown in FIG. 11. Bone screw 172 would extend into the sacrum when placed in the installed position in receiver 129 with implant 100 in the implanted position shown in FIG. 11.

Once implant 100 is fixed in the desired fashion in implant receiving volume 164, the dissections are closed in any suitable fashion to complete the procedure. In particular, the lumbar fascia may be closed in any suitable technique and the subcutaneous tissues also closed in any suitable technique. The skin layers are then closed by any suitable technique such as with staples for example.

Referring to FIGS. 13-15, another example SI joint implant 1300 is shown together with a locking element 1301. Implant 1300 has a triangular configuration similar to implant 100 and includes an elongated base member 1302, an elongated first side member 1303, an elongated second side member 1304, and internal support structure including a first lateral beam 1315 and second lateral beam 1316. Implant 1300 also includes fusion passages 1308, 1309, and 1310 defined in the area between base member 1302, first side member 1303, and second side member 1304. Locking element 1301 is attached to implant 1300 by suitable fasteners (not shown) similar to the embodiment shown in FIGS. 1-6. Although not shown in the figures, it will be appreciated that locking element 1301 is adapted to receive suitable bone screws similar to screws 171 and 172 shown in FIG. 12 to help fix the locking element and implant in the desired position as described above in connection with implant 100.

Unlike implant 100, implant 1300 includes a number of markers 1305, each located in a respective through hole 1307 formed in the implant. These markers 1305 may comprise Tantalum, Tantalum alloys, or other suitable materials which are readily apparent in x-ray images and thus facilitate radiographic identification of implant placement and fusion as is known in the art.

The various components of an implant according to the present invention may be formed from any suitable material or combination of materials. Some forms of the implant may be machined from a single block of suitable material such as a suitable stainless steel or titanium alloy. Alternatively, the various members of the implant, such as base member 102, side members 103 and 104, and beams 115 and 116 of example implant 100 may be separately formed and welded together or otherwise connected in a suitable fashion to form the implant. Any biologically compatible material that may withstand the forces required for implantation and withstand the normal forces expected in the implanted position may be used to form an implant according to the present invention.

Due to the structure of an implant embodying the principles of the present invention, the base member and side members from which it is formed together with the internal support structure may be made relatively small in the implant plane. This allows relatively larger fusion passages (such as passages 108, 109, and 110 in the illustrated example) as measured in the implant plane.

The dimensions of an implant embodying the principles of the invention and the various elements which make up the implant may be selected based on the sacrum and ilium bone structure of the patient to receive the implant. Generally, the overall length dimension of an implant such as implant 100 along the longitudinal axis L may be approximately 10.0 millimeters (mm) to approximately 25.0 mm for most patients, while the overall width dimension along width axis W may be approximately 10.0 mm to approximately 30.0 mm for most patients. The thickness of an implant such as implant 100 as measured at the widest part of base member 102 (in the direction perpendicular to the plane defined by axis L and axis W may be approximately 6.0 mm to approximately 14.0 mm for most patients. The angle A (FIG. 4) may be approximately 0 degrees to 20 degrees and more preferably approximately 8 degrees to 12 degrees for most patients. The side members such as 103 and 104 in FIGS. 1-3 and beams such as beams 115 and 116 (where such beams are included in the implant structure) may be approximately 3.0 mm wide for example in the width dimension (perpendicular to the member or beam longitudinal axis. While the above dimensions and ranges will hold for most patients, it should be appreciated that an implant according to the present invention may include one or more dimensions outside the above ranges and values while still falling within the scope of the invention and the following claims.

As used herein, whether in the above description or the following claims, the terms "comprising," "including," "carrying," "having," "containing," "involving," and the like are to be understood to be open-ended, that is, to mean including but not limited to. Also, it should be understood that the terms "about," "substantially," "approximately," and like terms used herein when referring to a dimension or characteristic of a component indicate that the described dimension/characteristic is not a strict boundary or parameter and does not exclude variations therefrom that are functionally similar. At a minimum, such references that include a numerical parameter would include variations that, using mathematical and industrial principles accepted in the art (e.g., rounding, measurement or other systematic errors, manufacturing tolerances, etc.), would not vary the least significant digit.

Any use of ordinal terms such as "first," "second," "third," etc., in the following claims to modify a claim element does not by itself connote any priority, precedence, or order of one claim element over another, or the temporal order in which acts of a method are performed. Rather, unless specifically stated otherwise, such ordinal terms are used merely as labels to distinguish one claim element having a certain name from another element having a same name (but for use of the ordinal term).

In the above descriptions and the following claims, terms such as top, bottom, upper, lower, and the like with reference to a given feature are intended only to identify a given feature and distinguish that feature from other features. Unless specifically stated otherwise, such terms are not intended to convey any spatial or temporal relationship for the feature relative to any other feature.

The term "each" may be used in the following claims for convenience in describing characteristics or features of multiple elements, and any such use of the term "each" is in the inclusive sense unless specifically stated otherwise. For example, if a claim defines two or more elements as "each" having a characteristic or feature, the use of the term "each" is not intended to exclude from the claim scope a situation having a third one of the elements which does not have the defined characteristic or feature.

The above described preferred embodiments are intended to illustrate the principles of the invention, but not to limit the scope of the invention. Various other embodiments and modifications to these preferred embodiments may be made by those skilled in the art without departing from the scope of the present invention. For example, in some instances, one or more features disclosed in connection with one embodiment can be used alone or in combination with one or more features of one or more other embodiments. More generally, the various features described herein may be used in any working combination.

The invention claimed is:

1. An implant for effecting a fusion of an SI joint, the implant including:
   (a) an elongated base member having a base member longitudinal axis extending parallel to an implant width axis and perpendicular to an implant longitudinal axis, the base member longitudinal axis defining a base of a triangle in an implant plane defined by the implant width axis and implant longitudinal axis;
   (b) an elongated first side member extending along a first side longitudinal axis which defines a first lateral side of the triangle;
   (c) an elongated second side member extending along a second side longitudinal axis which defines a second lateral side of the triangle;
   (d) an internal support structure extending in the implant plane from the base member to the first side member and from the base member to the second side member; and
   (e) three or more fusion passages defined in an area between the first side member, second side member, and base member, each fusion passage extending along a thickness axis perpendicular to the implant plane and defining a respective open area through the implant.

2. The implant of claim 1 wherein the internal support structure includes two or more beams extending transverse to the implant width axis and which divide the area between the first side member, second side member, and base member into the three or more fusion passages.

3. The implant of claim 2 wherein the area of the three or more fusion passages in the implant plane comprises approximately 50% of an overall area of the implant in the implant plane.

4. The implant of claim 2 wherein the two or more beams include:
(a) a first lateral beam extending along a first lateral beam longitudinal axis from a first lateral beam base end connected to the base member to a first lateral beam forward end connected to the first side member; and
(b) a second lateral beam extending along a second lateral beam longitudinal axis from a second lateral beam base end connected to the base member to a second lateral beam forward end connected to the second side member.

5. The implant of claim 4 wherein the first lateral beam and the second lateral beam converge in a direction along the implant longitudinal axis from a forward end of the implant to the base member.

6. The implant of claim 1 further including:
(a) an elongated locking element;
(b) at least one fixation device receiver formed in the locking element; and
(c) a connector arrangement connecting the locking element to the base member in a locking position so that the longitudinal axis of the base member extends parallel to a longitudinal axis of the locking element.

7. The implant of claim 6 wherein:
(a) the base member includes an elongated channel extending parallel to the implant width axis; and
(b) the locking element includes a projection configured to be received in the channel of the base member when the locking element is connected to the base member in the locking position.

8. The implant of claim 6 wherein the connector arrangement includes:
(a) at least one fastener opening through the locking element, the at least one fastener opening extending along an opening longitudinal axis perpendicular to the longitudinal axis of the locking element;
(b) a fastener shoulder formed in the at least one fastener opening; and
(c) a threaded opening in the base member adapted to align with the at least one fastener opening when the locking element is connected to the base member in the locking position.

9. The implant of claim 6 wherein the at least one fixation device receiver is configured to receive a fixation device along a receiver opening extending at an acute angle to the implant longitudinal axis when the locking element is connected to the base member in the locking position.

10. The implant of claim 6 wherein:
(a) the locking element includes a first fixation device receiver and a second fixation device receiver;
(b) the first fixation device receiver is configured to receive a respective fixation device along a first receiver passage extending from a plane defining a top surface of the locking element to a plane defining a first side of the locking element; and
(c) the second fixation device receiver is configured to receive a respective fixation device along a second receiver passage extending from the plane defining the top surface of the locking element to a plane defining a second side of the locking element, opposite to the first side of the locking element.

11. The implant of claim 1 wherein:
(a) the first side member, second side member, base member, and internal support structure define a first joint face contact surface on one side of the implant plane and a second joint face contact surface on an opposite side of the implant plane; and
(b) the second joint face contact surface extends at an angle of between 5 and 20 degrees to the first joint face contact surface in a direction along the implant longitudinal axis from a forward end of the implant to the base member.

12. The implant of claim 11 further including a first retention feature formed on the first joint face contact surface and a second retention feature formed on the second joint face contact surface.

13. The implant of claim 12 wherein:
(a) the first retention feature comprises a number of first side ridges spaced apart along the implant longitudinal axis and extending parallel to the implant width axis; and
(b) the second retention feature comprises a number of second ridges spaced apart along the implant longitudinal axis and extending parallel to the implant width axis.

14. The implant of claim 1 wherein the elongated base member has a length dimension that is less than a dimension defined between a first point at which the first side longitudinal axis intersects the base member longitudinal axis in the implant plane and a second point at which the second side longitudinal axis intersects the base member longitudinal axis in the implant plane.

15. A method for effecting a fusion of an SI joint, the method including:
(a) forming a sacral side implant receiving surface in the sacral side of the SI joint;
(b) forming an iliac side implant receiving surface in the iliac side of the SI joint opposite the sacral side implant receiving surface, the sacral side implant receiving surface and the iliac side implant receiving surface defining an SI joint implant receiving volume for receiving an SI joint implant including,
(i) an elongated base member having a base member longitudinal axis extending parallel to an implant width axis and perpendicular to an implant longitudinal axis, the base member longitudinal axis defining a base of a triangle in an implant plane defined by the implant width axis and implant longitudinal axis,
(ii) an elongated first side member extending along a first side longitudinal axis which defines a first lateral side of the triangle,
(iii) an elongated second side member extending along a second side longitudinal axis which defines a second lateral side of the triangle,
(iv) an internal support structure extending in the implant plane from the base member to the first side member and from the base member to the second side member,
(v) the first side member, second side member, base member, and internal support structure defining a first joint contact surface on one side of the implant plane and a second joint face contact surface on an opposite side of the implant plane;
(vi) three or more fusion passages defined in an area between the first side member, second side member, and base member, each fusion passage extending along a thickness axis perpendicular to the implant plane and defining a respective open area through the implant along the thickness axis; and
(c) fixing the SI joint implant in the SI joint implant receiving volume in an implanted position in which the fusion passages extend transversely across the SI joint.

16. The method of claim 15 wherein the method further includes:
(a) while the SI joint implant is in the implantation position, attaching a locking element to a base member of the SI joint implant; and
(b) placing at least one surgical fastener through a receiver opening of the locking element so as to extend into the sacrum or ilium.

17. The method of claim 15 wherein the method further includes:
(a) while the SI joint implant is in the implantation position, attaching a locking element to a base member of the SI joint implant;
(b) placing a first surgical fastener through a first receiver opening of the locking element so as to extend into the sacrum; and
(c) placing a second surgical fastener through a second receiver opening of the locking element so as to extend into the ilium.

18. The method of claim 15 wherein the elongated base member has a length dimension that is less than a dimension defined between a first point at which the first side longitudinal axis intersects the base member longitudinal axis in the implant plane and a second point at which the second side longitudinal axis intersects the base member longitudinal axis in the implant plane.

19. An implant for effecting a fusion of an SI joint, the implant including:
(a) a base structure;
(b) an insertion end structure spaced apart from the base structure along an implant longitudinal axis;
(c) an elongated first side member extending along a first side longitudinal axis and defining a first lateral side of the implant;
(d) an elongated second side member extending along a second side longitudinal axis and defining a second lateral side of the implant spaced apart from the elongated first side member along an implant width axis which lies perpendicular to the implant longitudinal axis and together with the implant longitudinal axis defines an implant plane;
(e) an internal support structure extending in the implant plane from the base structure to the insertion end structure;
(f) two or more fusion passages defined in an area between the first side member, second side member, base structure, and insertion end structure, each fusion passage extending along a thickness axis perpendicular to the implant plane and defining a respective open area through the implant;
(g) wherein the first side member, second side member, base structure, insert end structure, and internal support structure define a first joint face contact surface on one side of the implant plane and a second joint face contact surface on an opposite side of the implant plane; and
(h) wherein the second joint face contact surface extends at an angle of between 5 and 20 degrees to the first joint face contact surface in a direction along the implant longitudinal axis from the insert end structure to the base structure.

* * * * *